US008005624B1

(12) United States Patent
Starr (10) Patent No.: US 8,005,624 B1
(45) Date of Patent: Aug. 23, 2011

(54) MEDICAL DEVICES AND TECHNIQUES FOR RODENT AND SMALL MAMMALIAN BASED RESEARCH

(75) Inventor: Eric William Starr, Allison Park, PA (US)

(73) Assignee: STARR Life Sciences Corp., Oakmont, PA (US)

( * ) Notice: Subject to any disclaimer, the term of this patent is extended or adjusted under 35 U.S.C. 154(b) by 1151 days.

(21) Appl. No.: 11/115,072

(22) Filed: Apr. 26, 2005

Related U.S. Application Data (60) Provisional application No. 60/565,708, filed on Apr. 26, 2004.

(51) Int. Cl.
*G01N 33/48* (2006.01)
*G01N 1/00* (2006.01)

(52) U.S. Cl. ............................................ 702/19; 422/50

(58) Field of Classification Search .................. None
See application file for complete search history.

(56) References Cited

U.S. PATENT DOCUMENTS

| | | | |
|---|---|---|---|
| 2,706,927 A | 4/1955 | Wood | |
| 3,167,658 A | 1/1965 | Richter | |
| 3,599,629 A | 8/1971 | Gordy | |
| 3,602,213 A | 8/1971 | Howell et al. | |
| 3,638,640 A | 2/1972 | Shaw | |
| 3,704,706 A | 12/1972 | Herczfeld et al. | |
| 3,720,199 A | 3/1973 | Rishton et al. | |
| 3,769,974 A | 11/1973 | Smart et al. | |
| 3,807,388 A | 4/1974 | Orr et al. | |
| 3,819,276 A | 6/1974 | Kiess et al. | |
| 3,833,864 A | 9/1974 | Kiess et al. | |
| 3,847,483 A | 11/1974 | Shaw et al. | |
| 3,880,006 A | 4/1975 | Poduje | |
| 3,910,701 A | 10/1975 | Henderson et al. | |
| 3,998,550 A | 12/1976 | Konishi et al. | |
| 4,013,067 A | 3/1977 | Kresse et al. | |
| 4,059,991 A | 11/1977 | Dybel et al. | |
| 4,086,915 A | 5/1978 | Kofsky et al. | |
| 4,091,803 A | 5/1978 | Pinder | |
| 4,167,331 A | 9/1979 | Neilsen | |
| 4,225,410 A | 9/1980 | Pace | |
| 4,237,447 A | 12/1980 | Clark, III | |
| 4,266,554 A | 5/1981 | Hamaguri | |
| 4,305,401 A | 12/1981 | Reissmueller et al. | |
| 4,350,165 A | 9/1982 | Striese | |
| 4,370,984 A | 2/1983 | Cartmell | |
| 4,380,240 A | 4/1983 | Jobsis | |
| 4,406,289 A | 9/1983 | Wesseling et al. | |
| 4,407,272 A | 10/1983 | Yamaguchi | |
| 4,407,290 A | 10/1983 | Wilber | |
| 4,407,298 A | 10/1983 | Lentz et al. | |
| 4,446,715 A | 5/1984 | Bailey | |
| 4,494,550 A | 1/1985 | Blazek et al. | |
| 4,621,643 A * | 11/1986 | New et al. .................... 600/331 |
| 4,700,708 A | 10/1987 | New, Jr. et al. | |
| 4,830,014 A | 5/1989 | Goodman et al. | |
| 5,035,508 A * | 7/1991 | Carter et al. .................. 356/416 |
| 5,396,893 A * | 3/1995 | Oberg et al. .................. 600/484 |
| 5,490,523 A | 2/1996 | Isaacson et al. | |
| 5,792,052 A | 8/1998 | Isaacson et al. | |
| 5,800,349 A * | 9/1998 | Isaacson et al. ............. 600/323 |
| 7,062,306 B2 * | 6/2006 | Benaron et al. ............. 600/323 |

FOREIGN PATENT DOCUMENTS

WO    WO 00/13575    *  3/2000

OTHER PUBLICATIONS

Cruz et al., Laboratory Animals, 1998, vol. 32, p. 18-22.*
Berkowitz, Investigative Ophthalmology & Visual Science, Sep. 1996, vol. 37, No. 10, p. 2089-2098.*
Sidwell et al., Antimicrobial Agents And Chemotherapy Feb. 1992, p. 473-476.*
Abbott, Nature, Apr. 1, 2004, vol. 428, p. 464-466.*
Leonard et al., Emergency Medicine Journal, 2003, vol. 20, p. 524-525.*
Carly et al., Sleep Research Online, 2001, vol. 4, No. 1, p. 7-12.*
O'Neil et al., Environmental Health Perspectives, vol. 56, pp. 11-22, 1984.*
Lemieux et al. (JMRI, 1996; 6:561-564).*
Bailey et al. (Seminars in Avian and Exotic Pet Medicine, 1998, vol. 7, No. 1, p. 53-60).*
Design of Pulse Oximeters, In the Institute of Physics Publishing, Bristol Philadelphia, 1997, Edited by J.G. Webster (200 pages).

* cited by examiner

*Primary Examiner* — Marjorie Moran
*Assistant Examiner* — Pablo Whaley
(74) *Attorney, Agent, or Firm* — Blynn L. Shideler; Krisanne Shideler; BLK Law Group (57) ABSTRACT

A method and system of supplying rodents, such as mice, to medical researchers pre-installs and/or embeds physiologic sensors onto or within the rodents prior to selling the modified rodents to the researchers. The specialty skills, such as small animal surgical and anesthesia skills and sensor placement and testing, are centralized in one organization rather than being spread about a collection of researchers. The subjects with preinstalled, pre-tested hardware, are sold to the researcher as needed. Communication hardware and software will be supplied for the user to convert their desktop computer into a wireless monitoring station. Additionally an external pulse oximeter for small rodents, such as mice, provides measurements on a hand or foot of the rodent with a sensor configured to avoid shunting around the rodent appendage, and configured for high heart rates (200-900 beats per minutes) of the subjects.

18 Claims, 9 Drawing Sheets

MEDICAL DEVICES AND TECHNIQUES FOR RODENT AND SMALL MAMMALIAN BASED RESEARCH

RELATED APPLICATION

The present application claims the benefit of provisional patent application Ser. No. 60/565,708 entitled "Medical Devices and Techniques for Rodent and Small Mammalian Based Research" filed Apr. 26, 2004.

BACKGROUND OF THE INVENTION

1. Field of the Invention

The present invention relates to medical devices and techniques for rodent and small mammalian based research, in particular rodents with physiologic sensors such as pre-embedded research related hardware and external rodent pulse oximeter systems.

2. Background of the Invention

In conducting research on small mammals, such as, most commonly mice, a researcher must spend time and money on designing and implementing the data collection methods and devices that will be required. For example, Researchers have been embedding heart pumps and other hardware into cows and various other animals for years. Small mammals provide other unique problems for similar research. However it has been proposed for mice research to utilize embedded EEG electrodes and embedded electrode amplifiers with an embedded power supply all located within a mouse's skin. In this configuration an antenna protrudes from the mouse's head and EEG data is transmitted wirelessly from the antenna to a host computer for monitoring the mouse's brain activity.

There are several drawbacks with the existing procedures for performing research on small rodents. First, researchers must spend considerable time developing the tools to conduct their research instead of focusing on the specified research itself. This wasted set up time significantly delays the subsequent research, which is an impediment to the general progress of science and potentially very costly in competitive commercial areas.

Second, researchers will unduly waste materials in the development of the specialized tools. For example, in embedding hardware in small mammals, such as mice, the researcher's unfamiliarity with the devices and with the specific effect of anesthetic on the small mammals can lead to a very high morbidity rate. Loss rates as high as 33% for such procedures on mice would not be unexpected. Consequently, in this example, the researchers would have to spend time to design the desired embedded sensor configuration, develop a technique for applying the sensor and transmitter and power supply within the subject animals, purchase the equipment and animals in excess of what was needed due to loss rates, perform the operation for embedding the hardware in excess of what was needed due to loss rates, test the surviving embedded subjects to see which have the sensors working properly until enough validated test subjects are obtained to begin the study. There is a great need in the research area to reduce or eliminate such lead times, particularly in rodent based research such as mice based research.

There are certain companies that have attempted to address some of these concerns. Charles Rivers Labs acts as a service provider and offers a surgical process for implanting devices in small mammals, specifically rats, mice and guinea pigs. The various processes are performed by trained technicians, which can help reduce the loss rates. Specifically Charles Rivers Labs list the ability to provide blood pressure sensors, electrocardiograph sensors, electroencephalograph sensors, electromyography sensors, osmotic/infusion pump, vascular access port and small injectable devices in at least one of rats, mice or guinea pigs. Charles Rivers Labs will only operate on animals purchased from Charles Rivers Labs. Further, the devices to be implanted are the responsibility of the customer, who must select the appropriate sensor and advise Charles Rivers Labs of the sensor (and the desired sensor location). There is a very limited selection of device implantation processes that Charles Rivers Labs identifies for the customers, and of those listed only three (implantation of "osmotic/infusion pump", "vascular access port" and "simple injectable device") are available for mice. Charles Rivers Labs is willing to perform specialty operations. The services provided by Charles River Labs, and possibly other service providers, can reduce yield loss, but it does little to reduce lead time for research. The researcher must still identify and locate the desired sensor and sensor location on the mammal and then provide this material to a service provider, such as Charles Rivers Labs. Certain service providers, such as Charles Rivers Labs, limit the source of the animals further restricting the researcher.

The above stated problems are not limited to internal or embedded hardware devices for research in small mammals. Consider the problems associated with external physiologic sensors that are useful for research, such as oximeter and pulse monitoring technology, when applied to small mammals such as mice. These technologies are also of significant interest to researchers of small mammals as well, but the application of this technology to small mammals presents numerous difficulties. The inventor has identified that one of the most common difficulties with designing or implementing existing sensors for small mammal research is sensor sizing and placement in order to assure quality physiologic signals.

Figure 1:
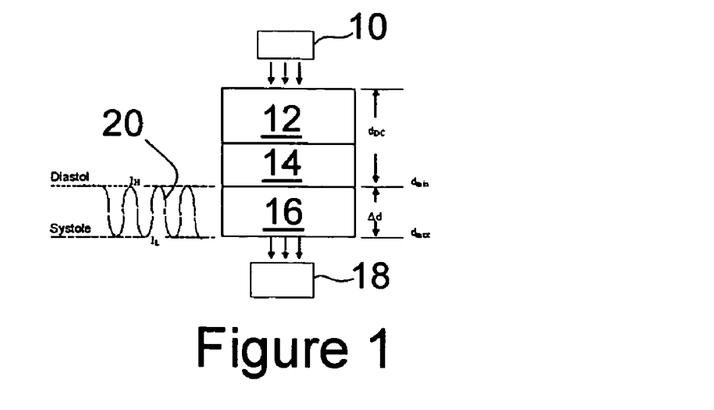
FIG. 1 schematically illustrates the photoplethysmographic phenomenon as generally known in the art.

As background, one type of non-invasive physiologic sensor is a pulse monitor, also called a photoplethysmographs, which typically incorporates an incandescent lamp or light emitting diode (LED) to trans-illuminate an area of the subject, e.g. an appendage, that contains a sufficient amount of blood. FIG. 1 schematically illustrates the photoplethysmographic phenomenon. The light from the light source 10 disperses throughout the appendage, which is broken down in FIG. 1 into non-arterial blood components 12, non-pulsitile arterial blood 14 and pulsitile blood 16, and a light detector 18, such as a photodiode, is placed on the opposite side of the appendage to record the received light. Due to the absorption of light by the appendage's tissues and blood 12, 14 and 16, the intensity of light received by the photodiode 18 is less than the intensity of light transmitted by the LED 10. Of the light that is received, only a small portion (that effected by pulsitile arterial blood 16), usually only about two percent of the light received, behaves in a pulsitile fashion. The beating heart of the subject creates this pulsitile behavior. The "pulsitile portion light" is the signal of interest and is shown at 20, and effectively forms the photoplethysmograph. The absorption described above can be conceptualized as AC and DC components. The arterial vessels change in size with the beating of the heart. The change in arterial vessel size causes the path length of light to change from $d_{min}$ to $d_{max}$. This change in path length produces the AC signal 20 on the photo-detector, $I_L$ to $I_H$. The AC Signal 20 is, therefore, also known as the photo-plethysmograph.

The absorption of certain wavelengths of light is also related to oxygen saturation levels of the hemoglobin in the blood transfusing the illuminated tissue. In a similar manner to the pulse monitoring, the variation in the light absorption caused by the change in oxygen saturation of the blood allows for the sensors to provide a direct measurement of arterial oxygen saturation, and when used in this context the devices are known as oximeters. The use of such sensors for both pulse monitoring and oxygenation monitoring is known and in such typical uses the devices are often referred to as pulse oximeters. These devices are well known for use in humans and large mammals and are described in U.S. Pat. Nos. 4,621, 643; 4,700,708 and 4,830,014 which are incorporated herein by reference.

With the above background, the researcher working with small mammals, in particular mice, is faced with several daunting questions when applying this technology to the desired subjects. The first question that people skilled in the art of human-based pulse oximeters ask is where do you put an oximeter sensor on a mouse? The problem is that a mouse's appendages and other hairless areas are smaller than the light emitters and light detectors employed in the external sensors. This causes light shunting on the appendages. Further, most manufacturers provide a light path to the photodiode, i.e. a window, that has larger dimensions than the photodiode itself. This may be done in order to make sure that that light that can enter the photodiode from the sides (up to an angle of 180 deg). This increases the shunting problems, particularly with small rodents.

Figure 2:
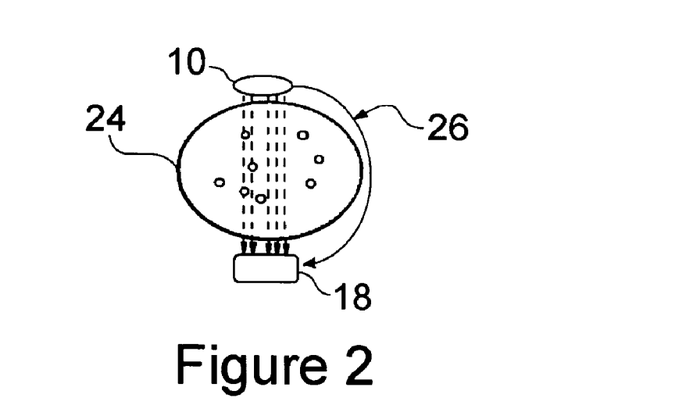
FIG. 2 schematically illustrates optical shunting in a pulse oximeter in which light from the emitter reaches the detector without passing through a subject's appendage.
Figure 3:
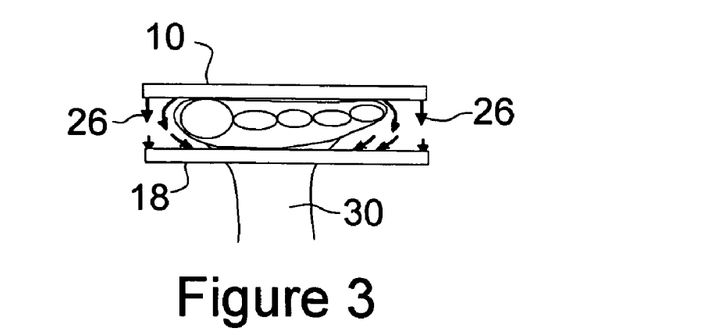
FIG. 3 schematically illustrates a conventional human infant pulse oximeter applied the foot or paw 30 of a mouse and illustrating the associated shunting problem therewith.

Optical shunting in pulse oximeters is schematically shown in FIG. 2 and occurs when light from the emitter 10 reaches the detector 18 without passing through an appendage 24. Shunted light 26 is a portion of the total transmitted light that passes around the appendage 24 directly to the detector 18. Since shunted light 26 simply passes by the appendage 24, the appendage's tissue does not absorb it. If light shunting occurs, it creates an enormous amount of noise, or extraneous signal, in a photo-plethysmograph. When attempting photo-plethysmograph-based measurement on tiny subjects, such as rodents and in particular mice, light shunting is an enormous challenge. FIG. 3, illustrates the same emitter 10 and photodiodes 18 that have been utilized in the typical neonatal human sensors discussed above and applied the foot or paw 30 of a mouse. The emitter 10 and detector 18, illustrated in FIG. 3, are the same emitter and detector illustrated in FIG. 2, specifically a human infant pulse oximeter such as the type sold by NELLCOR under the trademark Oxisensor® II. As illustrated in FIG. 3, emitters 10 and detectors 18 utilized for humans will not work for mice and small rats because the fingers, toes and even the entire feet or paw 30 of these subjects are so small that significant optical shunting is unavoidable.

There is a further problem with other possible locations for the existing pulse oximeters sensors for small mammals such as mice. Unlike in humans, the remainder of a mouse's outer body, other than the hands and feet, is covered with hair. Hair attenuates the pulsitile light signal that is needed in order to calculate SpO2 (i.e. the blood oxygenation).

In addition to where to locate an appropriate pulse oximeter on a small rodent, there are other unique problems. If the rodent subject is not anesthetized, in a very short period of time, the rodent will destroy the sensor or sensor cable by biting it. Further, mice have extremely high heart rates (200 to 900 beats per minute). The existing sensors and associated software do not accommodate such rates. These extremes can be passed off as noise in existing oximeter sensors used on humans and large mammals, thereby effectively discarding the signal of interest. The inability to effectively use existing sensors on mice and small rodents have led certain companies to exclude their oximeters for use on small (or very small) mammals. For example, Kent Scientific sells a pulse oximeter for "use with small animals" and the device clearly states that "the available sensor will not work with mice", which is particularly un-helpful for researchers utilizing mice.

It should be noted that an FFT-based measurement of respiratory rate using the same photoplethysmographic sensor that is utilized for pulse oximetry measurements has been tried/described by several researchers for humans and small mammals such as a dog or cat (see U.S. Pat. No. 5,396,893). Adult humans have respiratory rates in the range of 8 to 60 breaths/min. Adult humans have a heart rate in the range of 40 to 180 beats/min. Overall, the respiratory rate of humans is usually about ⅙ the heart rate. For example if a human is breathing at about 10 breaths per minute, the heart rate is usually somewhere around 60 beats per minute. Small mammals, such as mice and rats have a heart rate in the range of 200 to 900 beats/min. The respiratory rate of small mammals is also usually about ⅙ the heart rate. For a rat with a heart beat of 300 beats per minute, the respiratory rate is usually somewhere around 50 breaths per minute. The complex techniques for obtaining the respiratory rate from pulse oximetry sensors of the prior art simply do not translate to small mammals, such as mice.

There is a need in the industry to address the aforementioned drawbacks. There has also been a need to properly identify the drawbacks themselves as listed above, since once the failings of the prior art are properly identified the solutions thereto are more easily developed. There remains a need in the art to provide a simple, universal, cost effective system for providing medical devices for rodent based research applications. There remains a need in the art to provide a simple, cost effective, external mouse and small mammal pulse oximeter system for researchers. Various other objectives and advantages of the present invention become apparent to those skilled in the art as a more detailed presentation of the invention is set forth below.

SUMMARY OF THE INVENTION

A method of supplying rodents with pre-installed physiologic sensors, such as mice, to medical researchers according to the present invention addresses many of the problems with the above cited prior art. The present invention is to pre-install and possibly embed the physiologic sensors onto or within the rodents prior to selling the rodents with attached or embedded sensors to the researcher. The specialty skills, such as small animal surgical and anesthesia skills, sensor selection, implantation procedure, engineering, sterilization techniques, validation techniques, and all the hardware and software are centralized at a single source or single organization rather than being spread about a collection of researchers. It is contemplated that the majority of the embedded sensors will be of the wireless physiologic hardware. Further, it is anticipated that the embedded sensors may be entirely subcutaneous (below the subjects skin), as opposed to having an antenna stick through the subject's skin. The subjects, such as mice, with preinstalled, pre-tested hardware, are sold to the researcher as needed and when needed and in the quantity desired. In addition to the hardware embedded inside the animal, communication hardware and software will be supplied for the user to convert their desktop computer into a wireless monitoring station.

Another aspect of the present invention relates to external pulse oximeter in small rodents such as mice. The present invention provides a method and apparatus in which excellent results are obtained through taking measurements on a hand or foot of the rodent with a sensor configured to avoid shunting around the rodent appendage.

One aspect of the rodent pulse oximeter according to the present invention is sizing and shaping of the emitter and detector package to align with and conform to the shape of the rodents paw (hand or foot). Another embodiment of the rodent pulse oximeter according to the present invention provides for reducing the effective area of the emitter and detector currently utilized in human photo-sensors with a simple restricting adapter. A further aspect of the rodent pulse oximeter according to the present invention relates to the collimating of the light as it leaves the emitter, or as it approaches the detector, by using the depth of the restricting adapter. Further collimating the light may be obtained by adding a reflective surface to the inner wall of the restrictive adapter. Another feature of the rodent pulse oximeter according to the present invention is increasing the light transmission to/from the appendage by filling the aperture of the restrictive adapter with gel that approximates the refractive index of the rodent's skin. Another aspect of the rodent pulse oximeter according to the present invention is collecting more light from the emitter and detector used in human photo-sensors by adding at least one lens to the restrictive adapter. Another aspect of the rodent pulse oximeter according to the present invention is collecting more light from the emitter and detector used in human photo-sensors by adding an ellipsoidal reflector to the restrictive adapter. A further aspect of the rodent pulse oximeter according to the present invention is that the present invention measures saturation and pulse rate for rates between 200 and 900 BPM. Any heart beats greater than 900 BPM or less than 200 BPM are attenuated and/or ignored. The present invention further includes a simple effective system to protect the external sensor from being removed by the subject, and this protective system can be used with any similarly placed or situated sensors. The organization that supplies the modified rodents can transport rodents, such as mice, with the external sensors pre-attached, validated and calibrated as needed, with the protective system, such as a bootie, preventing the rodent from damaging or removing the sensor. The sensor can be left in place for a relatively long time and does not need to be attached by the end user.

Another aspect of the present invention relates to pulse oximetry in mice. The present invention provides a method and apparatus in which excellent results are obtained through taking measurements through the head of the mouse subject by placing the emitting and receiving sensors in the mouse's ears. These are not surgically implanted sensors, but similar to a rectal sensor, is not considered completely external to the subject for the purposes of this application.

These and other advantages of the present invention will be clarified in the detailed description of the preferred embodiment taken together with the attached drawings wherein like reference numerals represent like element throughout.

DESCRIPTION OF THE PREFERRED EMBODIMENTS

Figure 4:
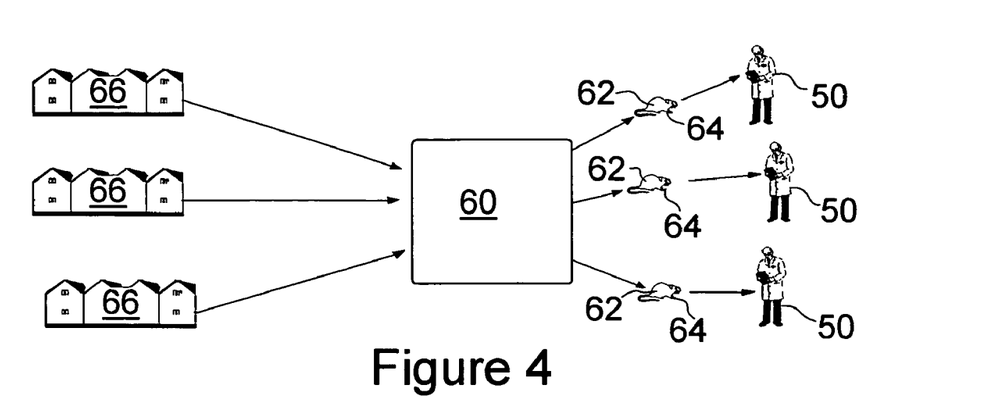
FIG. 4 is a schematic of the organizational arrangement for method of supplying rodents, such as mice, to medical researchers according to the present invention that will provide pre-installed and/or embedded physiologic sensors onto or within the rodents to the researchers.

FIG. 4 is a schematic of the organizational arrangement for method of supplying rodents, such as mice, to separate independent medical and other researchers 50 according to the present invention. The present invention will provide pre-installed and/or embedded physiologic sensors onto or within the rodents to the researchers 50. The key aspect of this portion of the invention is removing the design and implementation of the specific modified rodents from the individual researchers 50. The design step including selecting the appropriate sensors, locating and/or adapting them for use on the subject small rodents, developing the manufacturing techniques, the sterilization techniques, the validation techniques and all of the associated hardware and software needed. A single organization 60 will design a wide variety of modified rodents 62. Each style of rodent 62 will essentially be a rodent with a given physiologic sensor 64, or set of sensors 64 associated therewith. The implanted rodents 62 will be validated to be sure a valid, calibrated (where needed) signal is being obtained from the associated sensor(s) 64. The rodent 62 may further include the software needed to receive meaningful data. Most preferably the data will be able to be communicated with conventional laptop computers. It is anticipated that the organization 60 will deal with a variety of sensor vendors 66 as well as possibly a number of venders 66 for the specific rodents.

The present invention is not intended to be limited to specific rodents 62. The types of physiologic sensors 64 include, for example, Blood pressure sensors, blood flow sensors, Blood glucose sensors, Blood cholesterol sensors, heart sound sensors, EMG sensors, EEG sensors, EKG sensors, EOG sensors, Pulse sensors, Oxygenation sensors, blood perfusion sensors, respiration monitors (both flow and rate), temperature sensors, additional Blood gas sensors (such as nitrogen partial pressure, carbon dioxide partial pressure, carbon monoxide partial pressure and oxygen partial pressure PH Level or balance), motion sensors, strain gauges, body position sensors, limb motion sensors and the like. Through concentration only on providing modified rodents 62 with pre-installed physiologic sensors 64, the organization 60 will be able to focus on obtaining the most appropriate sensor 64 for each physiologic concern and can address and solve the unique problems associated with adapting the given sensor 64 for use on a small rodent such as a mouse. The details below regarding the particulars of a rodent pulse oximeter 70 according to the present invention will highlight this aspect.

The method of supplying modified rodents 62, such as mice, to independent researchers 50 provides further advantage where some, or the majority of, the embedded sensors 64 will be of the wireless physiologic hardware. The embedding of sensors 64 requires the acquisition of specialty skills, such as small animal surgical and anesthesia skills and sensor placement and validating or testing, in addition to those listed above. The present invention allows these skills to be rapidly obtained by the organization 60 since the manufacture of the entire "catalog" of modified rodents 62 is centralized in one organization 60, rather than being spread about a collection of researcher's organizations 50. The modified rodents 62 are created and the installed physiologic sensors 64 will be tested prior to sale of the modified rodent 62 to the researchers 50. In addition to the hardware (sensors 64) embedded inside or coupled to the modified rodents 62, communication hardware and software may be supplied for the user to effectively convert their desktop or laptop computer into a wireless monitoring station, such as through use of Bluetooth or Wi-Fi wireless standard technology.

The present invention provides a larger advantage than merely a reduction in the yield loss of subject rodents due to a centralized knowledge base in this area. The present invention rapidly advances the timetables for research involving small rodents. The researcher no longer must spend any time in designing the tools for a given study (i.e. the type of physiologic sensors required and the design of retrofitting existing sensors onto rodents for a particular study) and then actually building these tools. Followed by validating the newly designed tools are providing the meaningful data, which is all done prior to beginning the identified experiment. It is not unusual that the set up take as long as the actual experiment itself.

The advantages of the above described method of the present invention may be clarified in reviewing the details and advantages of an external pulse oximeter 70 of the present invention that is designed for small rodents, such as mice. The external pulse oximeter 70 provides excellent clinical results through taking measurements on a hand or foot (collectively the paw 30) of the rodent 62 with the emitter 10 and/or the receiver 18 configured to avoid shunting around the rodent appendage 30.

Figure 5:
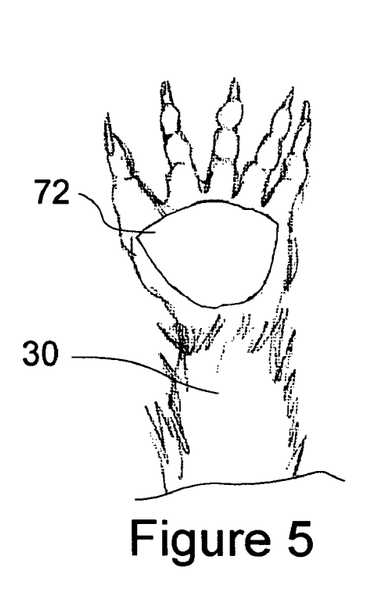
FIGS. 5 and 6 schematically illustrate the optimum area for light transmission for pulse oximeters in rodents.
Figure 6:
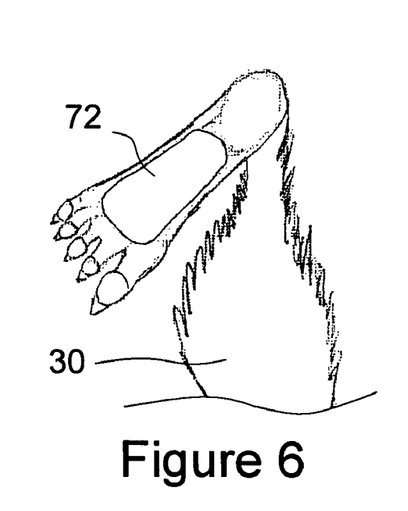

Though several iterations of painstaking trial and error, the present invention has established that the best locations (shown as 72 in FIGS. 5 and 6) to conduct external photo-plethysmograph-based measurements on a small rodent, such a mouse are the palm of the hand and the area between the heal and the ball of the foot, collectively referred to as the paw 30. FIGS. 5 and 6 illustrate these locations. These locations 72 are best because they are largest and meatiest, perfuse areas outside the body of the small rodent 62 that are not covered with hair. As stated above, the locations 72 require eliminating optical shunting. The locations 72 are sized to eliminate shunting. In other words, the light from the emitter 10 and or the light received in the receiver 18 should be restricted to the area of the illustrated location 72. Certain bench tests of the present invention have suggested that best results are achieved with a restricting adapter on the receiver or detector portion. The illustrated locations 72 also maximizes the cross sectional area of light passing through a perfuse appendage or paw 30 without creating a shunting problem which is done in order to maximize the photo-plethysmograph signal 20. In an appendage as thin as a mouse's paw 30, there is only a tiny total volume of blood that pulsates through the appendage with each heartbeat. Since the total pulsitile volume of blood is tiny, in order to create a resolvable photoplethysmographic signal 20, it is extremely important to pass the light beam through a high percentage of the total pulsitile volume available. The thickness of the paw 30 cannot be changed. Therefore, in order to maximize the volume of blood passing within the light beam, the surface area of light cast on the paw 30 must be maximized.

As can be seen in FIG. 5, although a simple circular or square-shaped beam can be used to transmit light through the hand or paw 30, utilizing the outline of the meaty part of the hand to create the border of the location 72 maximizes the surface area. As illustrated in FIG. 6, although a simple rectangular-shaped beam can be used to transmit light through the foot, utilizing the outline of the meaty part of the foot that is not obstructed by the anklebone maximizes the surface area of location 72. The sizing of the emitter to the location 72 can take one of two forms. The first format is to actually manufacture the emitter and detector to the desired dimensions. This solution may become practical at large manufacturing volumes.

At smaller manufacturing volumes for the pulse oximeter 70, the emitter 10 and the detector 18 are the same as found in existing human infant oximeters. The second form of sizing the emitter 10 to the location 72 is shown in FIGS. 7-12 and uses a simple restricting adaptor 80 adjacent the emitter 10 and/or the detector 18 with the adaptor 80 having an aperture 82 essentially the same shape as the location 72 thereby reducing the effective area of the emitter 10 and detector 18 currently utilized in human photo-sensors. The adaptor 80 may be formed of any material that does not transmit light there-through and in which an appropriate aperture 82 can be formed. One suitable material is light absorbing blackout material which is commercially available from Edmond Industrial Optics. Common black electrical tape has also proved satisfactory and relatively easy to work with. Light absorbing foam material is also acceptable for the adaptor 80.

Figure 7:
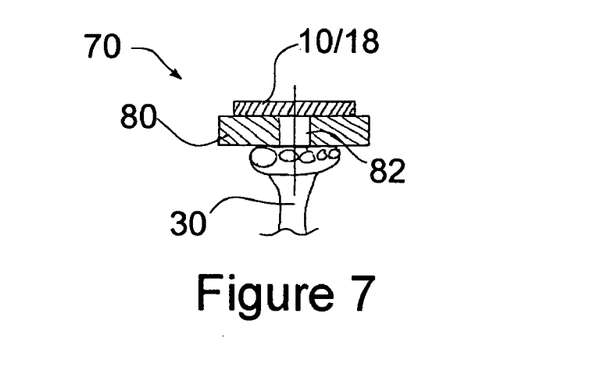
FIG. 7 schematically illustrates a sectional view of an emitter or detector for a rodent pulse oximeter including a collimating restricting adaptor according to the present invention.
Figure 8:
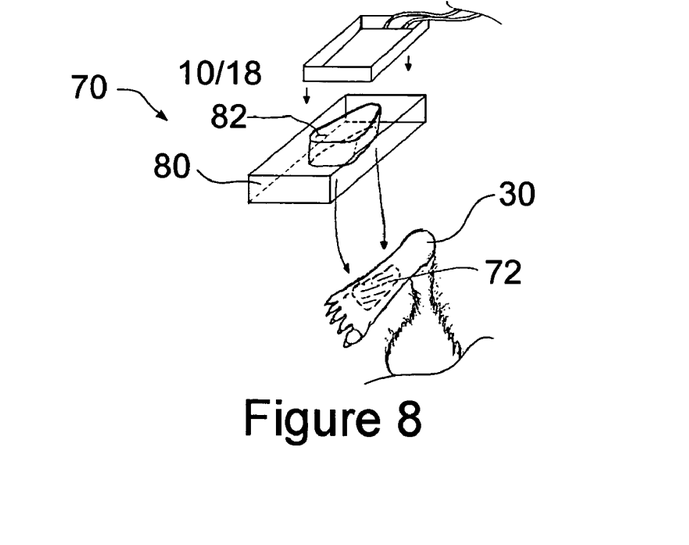
FIG. 8 is a schematic perspective partially exploded view of the emitter or detector for a rodent pulse oximeter including a collimating restricting adaptor as shown in FIG. 7.

The adapter 80 could also be used to recess the emitter 10 from the target area of the paw 30. Recessing the emitter 10 could redirect the light leaving the sides of the emitter 10 to a forward orientation. This, in certain applications, could result in a reduced angle of incidence, and an increase of the light beam intensity. In other words the thickness of the adaptor 80 could, in theory, serve to collimate the light from the emitter 10 thereby increasing its intensity and increasing it's effectiveness. Providing a relatively thick adaptor as shown in FIG. 7 could therefore theoretically act to collimate the light from the emitter 10 and further reduce and eliminate shunting. Bench testing of certain embodiments of the present invention have, conversely, shown no significant increase in performance from recessed emitters and/or detectors at the wavelengths tested. Regardless, one desired thickness for the adapter 80 is generally about the thickness of conventional emitters 10. For simplicity, FIG. 7 illustrates only one half of the emitter 10 and detector 18 with adaptor 80 (i.e. it is only shown on one side of the foot or paw 30). However, is should be understood that the other half is placed on the opposed surface of the foot, with the first and second halves aligned. At least one half will utilize the adapter 80, however both halves (i.e. the emitter 10 and the detector 18) can benefit from a respective adapter 80. Again, bench tests of certain wavelengths have found best results with the adapter only on the side of the detector or receiver 18. In a prototype of the present invention a spring biased clip to hold both halves on the rodent's paw or foot. A top part of the clip may have a countersunk (angled) hole through it and the end may be painted black. This is done so that the photodiode only receives light that has passed through blood filled tissue. The hole is angled so that the entire photodiode surface is utilized even though we only allow light to be received through a small opening. Another version of this clip uses a shape that approaches the shape of the bottom of the foot or paw, instead of a simple circle, and will also implement a slot shaped opening that angles as needed to match the photodiode area. The prototype is only implementing the aperture reduction technique (angled hole) on the photodiode side of the clip. Through bench tests have suggested that better signals result from letting the LED's broadcast as much light as possible while capturing only the light that has passed through blood filled tissue by utilizing the angled hole to cover the photodiode. It is contemplated that the LED package and photodiode will be slipped into position on the clip. The user is able to replace the clip as often as needed, while reusing the LED package, photodiode and wires leading to them.

To reiterate, as suggested above, in order to get a good pulse signal from mice, rats & other small animals using light, the light must pass through tissue that has very little hair or the hair must be removed (shaved). This is because hair attenuates light. The areas of small animals that have very little or no hair are limited to the feet & ankles and wrists and hands (the appendages). These appendages are almost always smaller than the windows that Novametrix, Nellcor and other manufacturers have been utilized to date on their photodiodes (e.g. the receivers). Even worse, the smallest of subjects, mice & baby rats for example, have appendages that are even smaller than the photodiode dimensions itself. The problem is that if the window is bigger than the subject's appendage, ambient light is received by the photodiode. Ambient light cause tremendous amounts of noise in the pulse signal. In order to solve this problem, the present invention provides a window that is based on the expected range in size of subject's appendages. It is expected in implementing this invention commercially, more than one size window will be used (the smallest window for the smallest subjects and the largest window for the largest subjects). The largest window utilizes the exact same dimensions as the photodiode dimensions, and the smallest window is much smaller than these dimensions. This window may be employed directly in a sensor as manufactured, or this window will be employed in a sensor adapter as described above. The sensor adapter will be placed over existing manufacturer's sensors in order to allow them to be used on the appendages of mice, rats and other small subjects.

Figure 9:
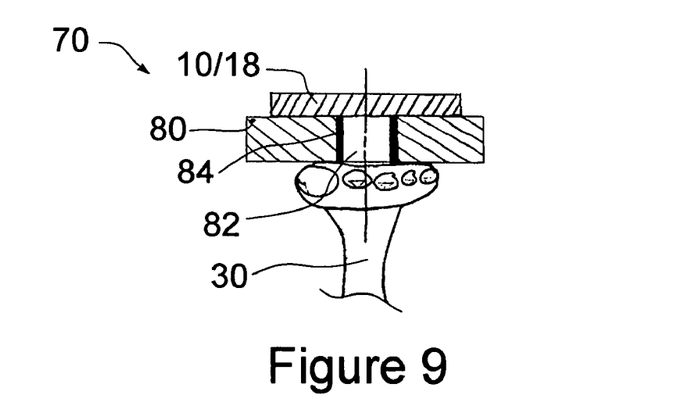
FIG. 9 schematically illustrates a sectional view of an emitter or detector for a rodent pulse oximeter similar to FIG. 7 and including a modified collimating restricting adaptor according to the present invention.

FIG. 9 schematically illustrates a sectional view of an emitter 10 or detector 18 for a rodent pulse oximeter 70 similar to FIG. 7 and including a modified collimating restricting adaptor 80 according to the present invention. In addition to simply recessing the emitter 10 and/or detector 18 to collimate the light, the inner surface of the aperture 82 recess can be constructed of, or covered with, a light reflective (i.e. a mirrored) material 84. Using reflective material 84 will further increase the intensity of the light on location 72 because light is reflected off the material 84 rather than being absorbed by the adapter 80.

Figure 10:
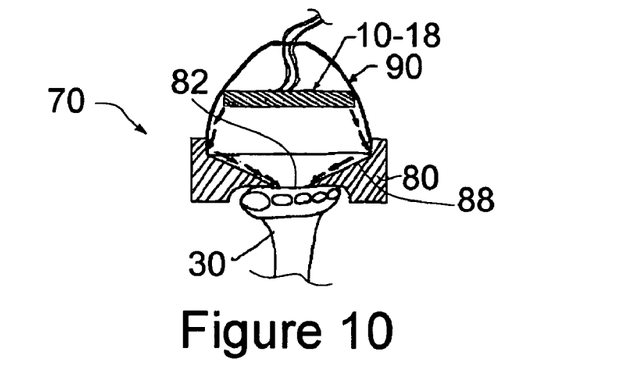
FIG. 10 schematically illustrates a sectional view of an emitter or detector for a rodent pulse oximeter similar to FIGS. 7 and 9 and including a modified restricting adaptor and reflector according to the present invention.

FIG. 10 schematically illustrates a sectional view of an emitter 10 or detector 18 for a rodent pulse oximeter 70 similar to FIGS. 7 and 9 and including a modified restricting adaptor 80 and reflector 90 according to the present invention. As shown in FIG. 10, adding an ellipsoidal reflector 90 to the light emitter 10 can further intensifies the light beam on the location 72. An important point concerning this configuration is that the outer surface 88 of the aperture 82 facing the emitter 10 should be angled to approximate the angle of reflection of the ellipsoidal reflector 90. The narrow portion of the aperture 82, or throat, is sized to match the location 72. As shown the opposed side of the aperture 82 may be formed to receive the paw 30 to assist in placement of the apparatus on the rodent.

Figure 11:
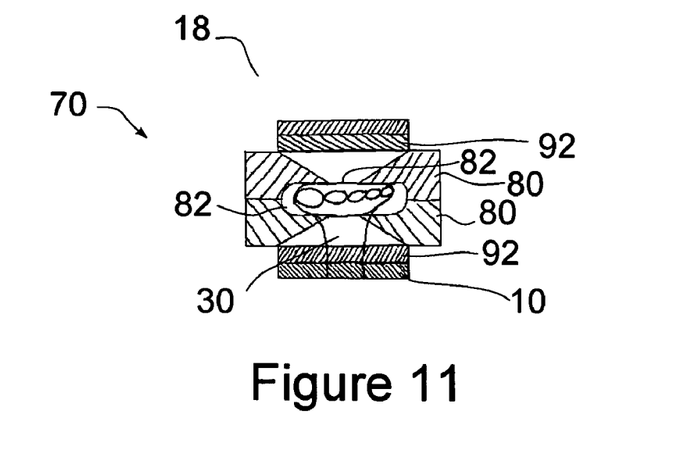
FIG. 11 schematically illustrates a sectional view of an emitter and detector for a rodent pulse oximeter similar to FIGS. 7, 9 and 10 and including a modified restricting adaptor and lens according to the present invention.

FIG. 11 schematically illustrates a sectional view of an emitter 10 and detector 18 for a rodent pulse oximeter 70 similar to FIGS. 7, 9 and 10 and including a modified restricting adaptor 80 and lens 92 in a clip arrangement according to the present invention. In order to maintain a compact assembly for the adapter and still transmit a very intense beam of light, a lens 92 can be added to the adapter 80. FIG. 11 illustrates how lenses 92 can be added to the adapter 80 so that in addition to reducing the effective aperture size of the emitter 10 and detector 18, the light beam is intensified. Again, an important point concerning this configuration is that the outer surface 88 of the aperture 82 (facing the associated emitter 10 or detector 18) should be angled to approximate angle of reflection of the lenses 92.

Figure 12:
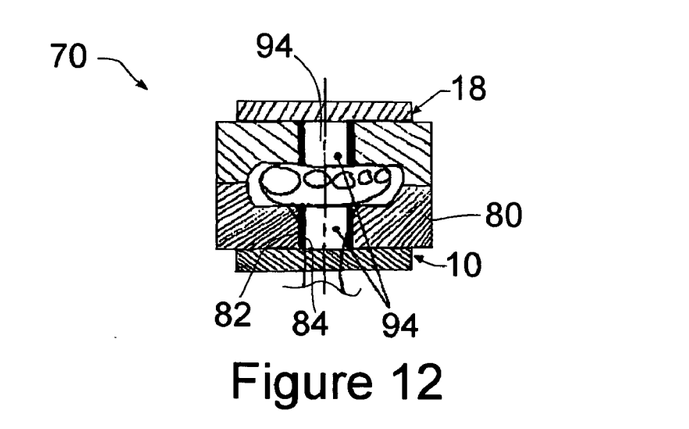
FIG. 12 schematically illustrates a sectional view of an emitter and detector for a rodent pulse oximeter similar to FIG. 9 and including a modified restricting adaptor according to the present invention.

FIG. 12 schematically illustrates a sectional view of an emitter 10 or detector 14 for a rodent pulse oximeter 70 similar to FIG. 9 and including a modified restricting adaptor 80 according to the present invention. The modification in FIG. 12 is the inclusion of a material 94 in the aperture 82 that has an index of refraction that approximates the index of refraction of either (1) the LED or photo-diode housing or (2) the rodent's skin. For example, if clear polycarbonate covers the diode, then the refractive index of the material 94 can approximate, or match, the refractive index of the polycarbonate. A sticky gel type material may be suitable for the material 94. A further alternative is to construct the material that has a refractive index that gradually changes in refractive index from that matching the refractive index of the diode housing to that matching the refractive index of the rodents skin. The use of sticky, viscous-elastic gel that has an index of refraction that approximates the index of refraction of a subject's skin for human applications has been designed for, and currently owned by Respironics Incorporated by the inventor concurrently with the present invention.

The rodent pulse oximeter 70 further includes filter cutoffs, roll-offs and software-based pulse acceptance criteria that are different than those employed in veterinary medicine and human oximeters. Specifically the oximeter 70 will measure saturation and pulse rate for rates between 200 and 900 BPM (beats per minute). Any heart beats greater than 900 BPM or less than 200 BPM are attenuated and/or ignored (i.e. a band pass filter for these set points is used). The most critical set point is eliminating results below 200 BPM. Dogs, cats and other medium sized mammals generally have lower heart rates than rodents and humans generally have lower heart rates than dogs and cats. Small rodents, such as mice, have a breathing rate that is in the general range of the heart rate for dogs, cats and other medium sized mammals. A "universal" oximeter (one designed to operate on small and medium and large mammals) would need a mechanism to determine whether a selected portion of the signal is noise (such as a rodents breathing when the rodent is the subject and the signal is being resolved for the heart rate) or is the signal of interest (i.e. the pulsitile signal of the subject when the signal is being resolved for the heart rate). The present invention uses a filter that filters out the noise associated with the breathing rate of the desired subjects. In other words the lower level of the filter is selected higher than the conventional breathing rates of small rodents in the oximeter according to the present invention. This manipulation of the resulting data helps makes the oximeter 70 unique to the small rodents such as mice.

Figure 13:
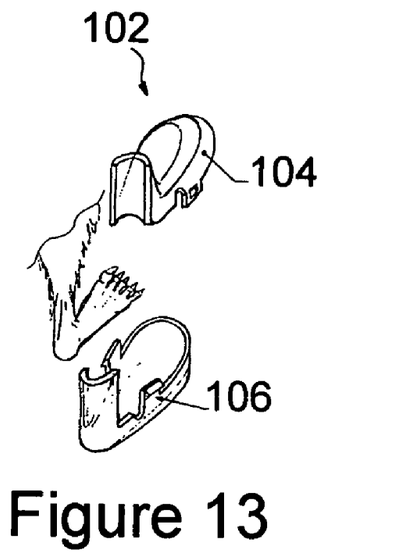
FIGS. 13 and 14 schematically illustrate exploded views of protective boots for the oximeter according to the present invention.
Figure 14:
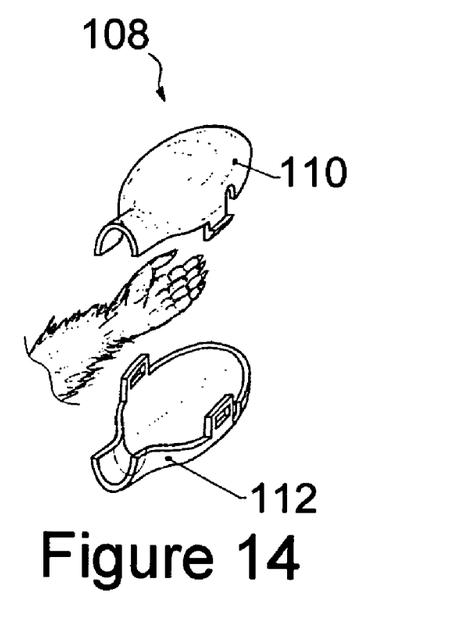
Figure 15A:
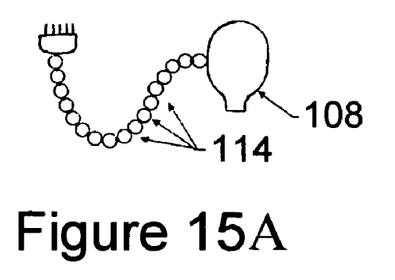
FIG. 15 is a schematic sectional view of a cord protecting system for wired sensors according to the present invention.
Figure 15B:
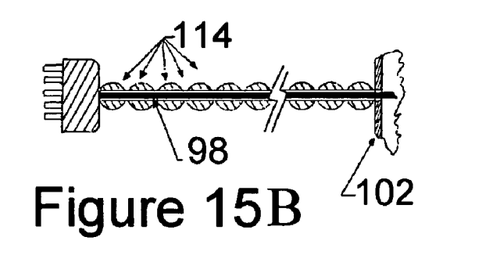
Figure 16A:
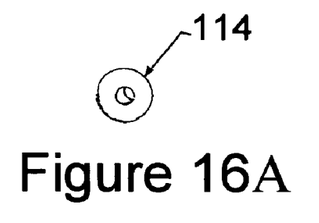
FIG. 16 is an exploded sectional view of the cord protecting system of FIG. 15.
Figure 16B:
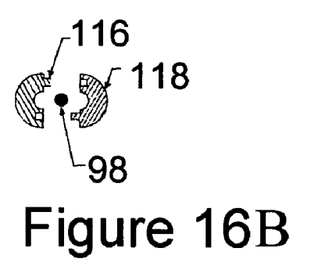

The oximeter 70 will have other features in it's implementation, such as, for example, oximeter sensor & cable chew-protection. A problem is that un-sedated mice and rats attempt to destroy an attached oximeter 70 and cable 98 by biting it. A further problem is that when a subject's appendage becomes cold, vessels constrict and the signal quality is reduced. A foot boot or bootie 102 having two snap on halve 104 and 106 as shown in FIG. 13 that covers the sensor 70 can be implemented to keep un-sedated mice, rats or other animals from biting the oximeter sensor 70. A similar hand boot or bootie 108 with halves 110 and 112 can be used for the hand as shown in FIG. 14. The cable 98 can be surrounded with protective snap on hard, wear resistant beads 114, formed of two bead halves 116 and 118 as shown in FIGS. 15-16. Alternatively, the sensor cable 98 can be covered with a sleeve of steel mesh or other material that cannot easily be chewed to protect the sensor cable 98. The booties 102 and 108 could also be used to warm the subject by retaining the heat emitted by the LED's thereby improving signal & measurement quality. This booties 102 and 108 could also contain a connector so that the bootie 102 or 108 can stay on the subject for long periods (such as during shipment of the rodent) when the oximeter 70 is not in use (i.e. disconnect the bootie from monitor cable when not in use).

Figure 17:
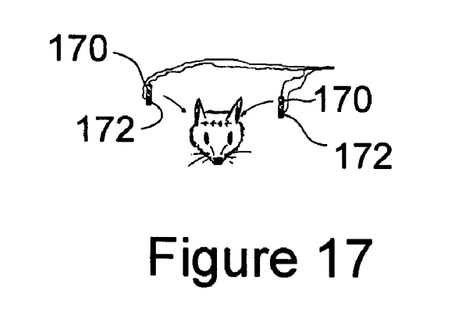
FIG. 17 is a schematic view of a mouse temperature and pulse oximeter sensor according to the present invention.

FIG. 17 illustrates a mouse temperature and pulse oximeter sensor 170 according to the present invention. In the sensor 170 the emitter and receiver are placed in the ears of the mouse subject. The size of a mouse allows the trans-illumination of the cranium between the ears, which is simply not possible for larger mammals. The placement allows for the detector or the emitter to include a temperature sensor 172. This location of the emitter and receiver or detector require specially sized sensors, however this sensor location does alleviate some of the problems encountered with mouse oximeters. Excellent results are obtained by taking measurements through the head of the mouse subject by placing the emitting and receiving sensors in the mouse's ears. These are not surgically implanted sensors and is therefore an "external" sensor, but similar to a rectal sensor, is not considered "completely" external to the subject for the purposes of this application.

Figure 20:
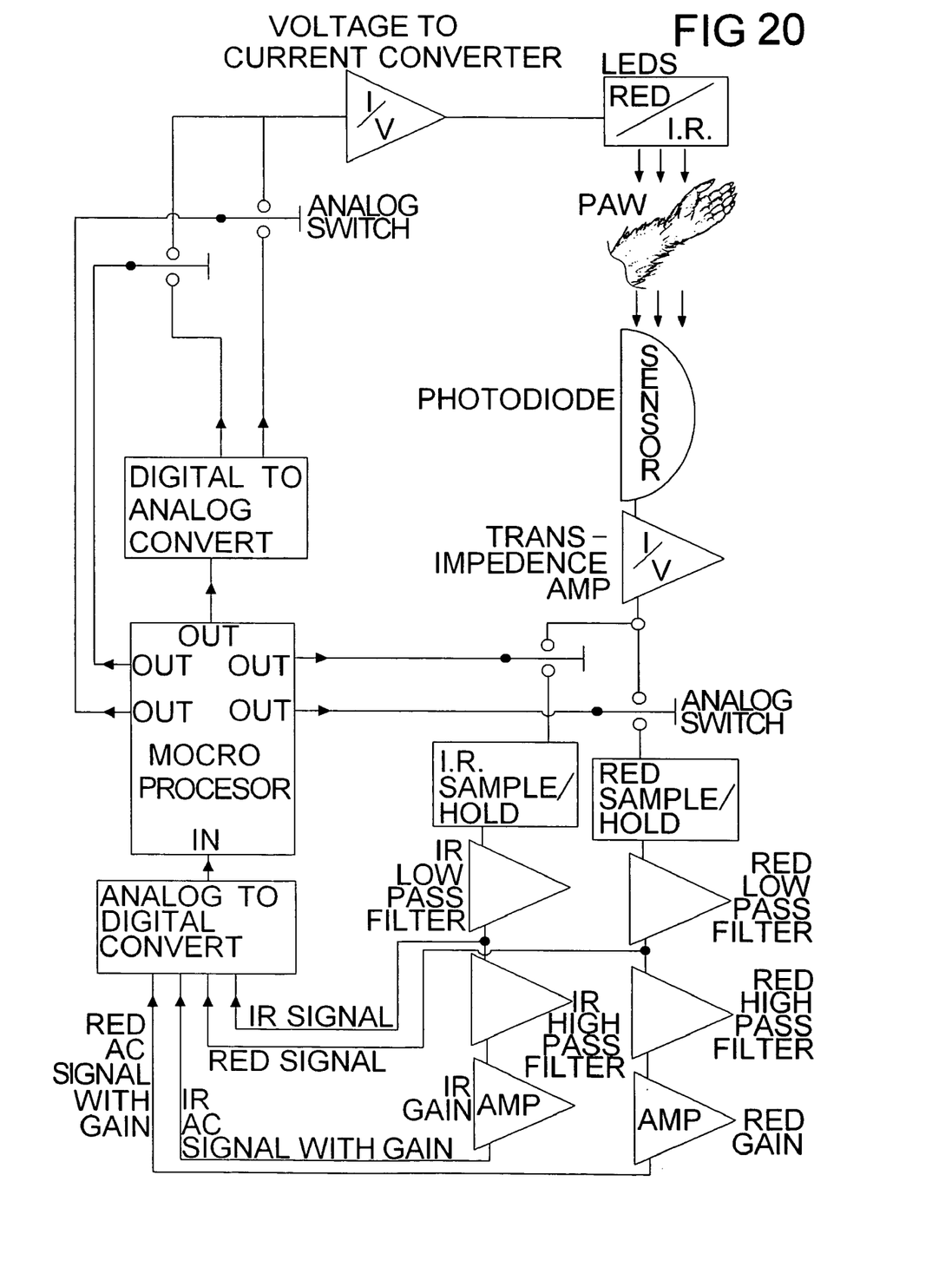
FIG. 20 is a schematic block diagram of sample electronic control for a small mammal pulse oximeter according to the present invention.

In the small mammalian pulse oximeter a measurement of respiratory rate can be achieved from the same photoplethysmographic sensor that is utilized for our pulse oximetry measurements of oxygen saturation and heart rate. In fact, all three of these measurements can be recorded simultaneously in the present invention. No components need to be added to the pulse oximeter sensor described above, which consist of 2 LED's (different wavelengths) and 1 photodiode. Further, no components need to be added to the pulse oximetry electronic circuits which consist of 2 LED current drivers a current to voltage converter for the photodiode, de-multiplexing electronics, band pass filtering and gain circuitry, analog to digital conversion electronics and a microprocessor (See FIG. 20).

Figure 18:
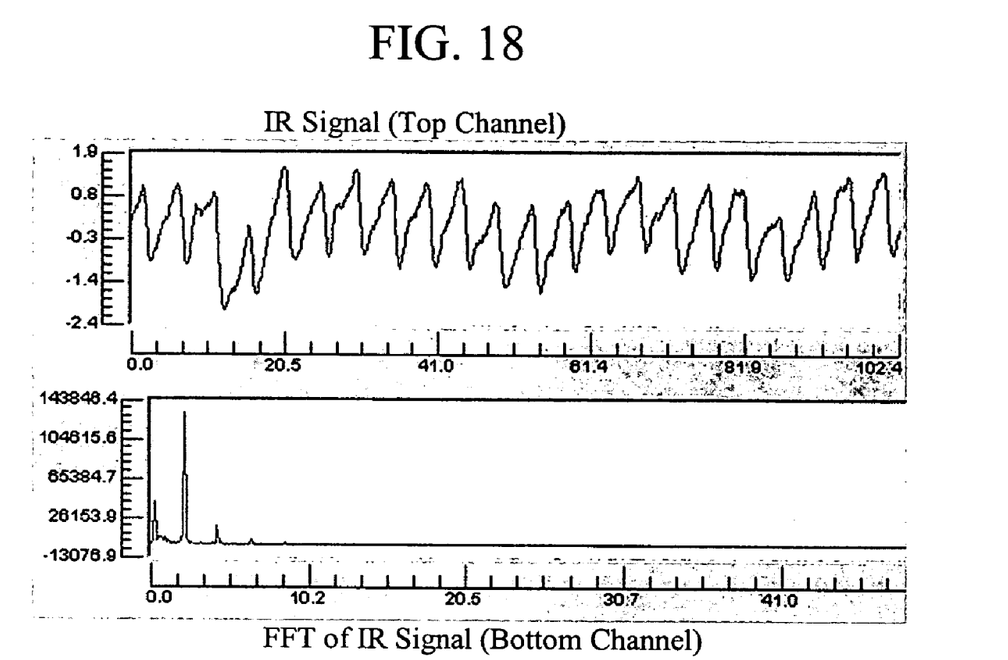
FIG. 18 is a graph of a representative signal from a photodiode of an IR emitter and a representative FFT thereof for a small mammal pulse oximeter according to the present invention.

The ways in which the present pulse oximeter achieves the respiratory rate measurement are comprised of the following steps:

A) Read one of the two light signals into an FFT, such as shown in FIG. 18. A 1024 sample FFT may be effectively used. Each light signal may be sampled at a rate of 300 samples/second and the light signal that is read into the FFT may be the infrared light signal (where an infrared and visible light source are used).

B) At least two big peaks will result in the FFT of the light signal (See FIG. 18). One of theses big peaks is the fundamental frequency of the breathing, a.k.a. the respiratory rate. The other of these big peaks is the fundamental frequency of the heart beating, a.k.a. the heart rate.

C) There are at least two methods to measure respiratory rate from the FFT. Both of these methods involve detecting at least one of the two big peaks contained within the FFT (i) The simplest way to measure respiratory rate from the FFT is to assume a frequency range in which the fundamental frequency of respiration will occur. This method inherently assumes that the fundamental frequency of the heart beating will not occur in this same range, which will work for small mammals. With these assumptions, a software algorithm is utilized to detect the one big peak within the range that the fundamental frequency of respiration is assumed to occur. The one big peak can be found by simply looking for the maximum value of the FFT signal within the frequency range that it is assumed to occur. (ii) A more robust way measure respiratory rate from the FFT is to assume that of the two or more big peaks contained within the FFT, the lowest frequency one is the respiratory rate. With this technique, the software algorithm must detect at least two peaks instead of only one peak. One way to identify more than one peak within the FFT signal is to calculate the first derivative of the signal by subtracting from each point the previous point. Every time a peak in the signal occurs the sign of the subtraction result will change from positive to negative. If the first derivative is calculated for every one of the 1024 samples within the FFT, every peak will be identified. The amplitude and frequency of each point where the result of the subtraction changed from positive to negative is then compared. The two or three highest amplitudes are the two or three biggest peaks in the FFT. The lowest frequency one of these two or three biggest peaks is the fundamental frequency of respiration.

Figure 19:
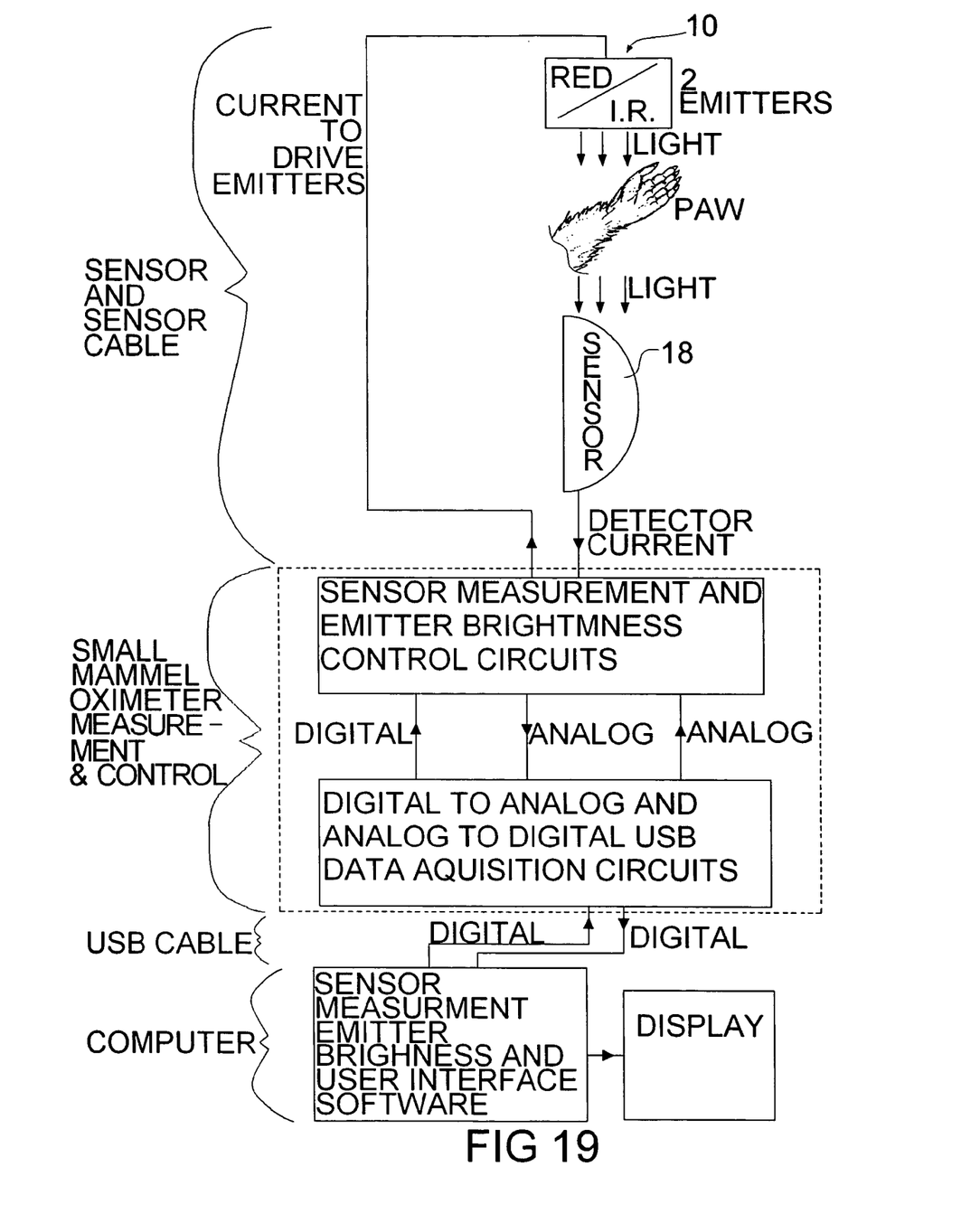
FIG. 19 is an architectural schematic block diagram of a small mammal pulse oximeter according to one aspect of the present invention.

D) Once the fundamental frequency of respiration is identified from within the FFT, it is converted from Hz to breaths/minute and displayed as respiratory rate (see the display in FIG. 19).

Although, small and large mammals share approximately the same multiplier from respiratory rate to heart rate, the difference between these two rates (heart rate—respiratory rate) is much greater for small mammals than for large mammals, for instance the difference in the human example given is only 50, while then difference in the rat example given is 250. Because the difference in rates is so much bigger for smaller subjects, the present invention can utilize the simple techniques described herein to measure the respiratory rate. The techniques described by prior researchers have been much more elaborate and have not been expanded to small mammal applications.

The described embodiment is intended to be illustrative of the present invention and not restrictive thereof. There are numerous modifications to the method, system and structures of the present invention that do not depart form the spirit and scope thereof, and the present invention is intended to be inclusive of these modifications. The scope of the present invention is defined by the appended claims and the equivalents thereto.

What is claimed is:

1. An external small mammal pulse oximetry system comprising:
   A) an emitter adjacent a small mammal, the emitter having two light sources of distinct wavelengths;
   B) a receiver adjacent the small mammal for detecting light from the emitter that has been transmitted toward a perfused tissue of the small mammal; and
   C) a controller to control the emitter and process signals from the receiver, wherein the controller is configured to receive a first and a second digital signal from the receiver associated with one distinct wavelength of light and to receive a first and a second digital signal from the receiver associated with the other distinct wavelength of light, and wherein the digital signals are utilized to determine the pulse rate of the small mammal and the blood oxygenation level of the small mammal, wherein the controller is configured to determine heart rate pulses of at least 450 beats per minute.

2. The external small mammal photoplethysmograph based pulse oximetry system according to claim 1 wherein the emitter and the receiver are configured to be placed on opposed ears of the small mammal whereby the light that is received by the receiver is transmitted through the head of the small mammal by the emitter.

3. The external small mammal pulse oximetry system according to claim 1 further including a bite resistant shell around the emitter and receiver, wherein the shell includes a pair of boot halves snapped together around both the emitter and the receiver.

4. The external small mammal pulse oximetry system according to claim 1 further including cables leading to the emitter and receiver and a bite resistant shell around the cables wherein the shell includes a plurality of protective beads snapped around the cables.

5. The external small mammal pulse oximetry system of claim 1, further including a restricting adaptor adjacent the receiver with the adaptor having an aperture smaller than the external dimensions of the receiver.

6. The external small mammal pulse oximetry system of claim 1, wherein the adaptor includes a mechanism to maximize the light transmitted through the aperture.

7. The external small mammal pulse oximetry system of claim 1, wherein the controller is configured to determine pulse rates of 500 beats per minute.

8. The external small mammal pulse oximetry system of claim 1, wherein the controller is configured to determine pulse rates of 600 beats per minute.

9. The external small mammal pulse oximetry system of claim 1, wherein the controller is configured to determine pulse rates of 700 beats per minute.

10. The external small mammal pulse oximetry system of claim 1, wherein the controller is configured to determine pulse rates of 800 beats per minute.

11. The external small mammal pulse oximetry system of claim 1, wherein the controller is configured to determine pulse rates of 900 beats per minute.

12. An external small mammal pulse detecting system comprising:
    A) an emitter adjacent the small mammal, the emitter having two light sources of distinct wavelengths;
    B) a receiver adjacent the small mammal for detecting light from the emitter that has been transmitted toward a perfused tissue of the small mammal; and
    C) a controller to control the emitter and process signals from the receiver, wherein the controller is configured to determine the pulse rates of the small mammal using the processed signals from the receiver, wherein the pulse rates are at least 450 beats per minute.

13. The external small mammal pulse oximetry system according to claim 12 wherein the controller is configured to process the signal from the receiver to determine the pulse rate of the small mammal, the blood oxygenation level of the small mammal and the respiration rate of the small mammal.

14. The external small mammal pulse detecting system of claim 12 wherein the controller is configured to determine pulse rates of 500 beats per minute.

15. The external small mammal pulse detecting system of claim 12 wherein the controller is configured to determine pulse rates of 600 beats per minute.

16. The external small mammal pulse detecting system of claim 12 wherein the controller is configured to determine pulse rates of 700 beats per minute.

17. The external small mammal pulse detecting system of claim 12 wherein the controller is configured to determine pulse rates of 800 beats per minute.

18. The external small mammal pulse detecting system of claim 12 wherein the controller is configured to determine pulse rates of 900 beats per minute.

* * * * *